US012661272B2

(12) United States Patent     (10) Patent No.:   US 12,661,272 B2

Loock     (45) Date of Patent:   Jun. 23, 2026

---

(54) PATCH FOR FEMALE GENITAL AREA

(71) Applicant: Cordula Loock, Schwabhausen (DE)

(72) Inventor: Cordula Loock, Schwabhausen (DE)

(73) Assignee: PAVAOO Medizinprodukte GmbH & Co. KG, Dachau (DE)

( * ) Notice: Subject to any disclaimer, the term of this patent is extended or adjusted under 35 U.S.C. 154(b) by 0 days.

(21) Appl. No.: 18/728,738

(22) PCT Filed: Jan. 12, 2023

(86) PCT No.: PCT/EP2023/050595

§ 371 (c)(1),
(2) Date: Jul. 12, 2024

(87) PCT Pub. No.: WO2023/135192

PCT Pub. Date: Jul. 20, 2023

(65) Prior Publication Data

US 2025/0107936 A1    Apr. 3, 2025

(30) Foreign Application Priority Data

Jan. 14, 2022   (DE) ..................... 10 2022 100 783.9
Oct. 19, 2022   (DE) ..................... 20 2022 105 871.7

(51) Int. Cl.
*A61F 13/02*    (2024.01)
*A61F 13/00*    (2024.01)
*A61H 19/00*    (2006.01)

(52) U.S. Cl.
CPC ........... *A61F 13/023* (2013.01); *A61H 19/34* (2013.01); *A61F 2013/00574* (2013.01)

(58) Field of Classification Search
CPC ................ A61F 13/00; A61F 13/00008; A61F 13/00021; A61F 2013/00089;
(Continued)

(56) References Cited

U.S. PATENT DOCUMENTS 5,336,208 A    8/1994   Rosenbluth et al.
5,628,724 A   *   5/1997   DeBusk ................ A61F 13/023
                                           206/440
(Continued)

FOREIGN PATENT DOCUMENTS

DE        69229719 T2    12/1999
DE    102020129363 A1    5/2022
(Continued)

OTHER PUBLICATIONS

Search Report received in German Application No. 10 2022 100 783.9 dated Sep. 27, 2022, with translation, 9 pages.
(Continued)

*Primary Examiner* — Ophelia A Hawthorne

(74) *Attorney, Agent, or Firm* — Christopher A. Rothe; CM Law

(57) ABSTRACT

A plaster for use in the female genital area of a user includes a plaster main film having a plaster inner surface that is covered at least partially by an adhesive layer. During use, the adhesive layer adheres to skin in the female genital area, and when not in use, is completely covered by a cover film. The plaster main film is dimensioned and configured so that, during use, it completely surrounds the urinary tract orifice of the user while enclosing particularly at least the major part of the labia majora and minora of the user, and at the same time leaves open the vaginal entrance of the user.

27 Claims, 4 Drawing Sheets

(58) Field of Classification Search
CPC .... A61F 2013/15121; A61F 2210/0014; A61F
2250/0036; A61F 2250/0078; A61F
13/02; A61F 13/472; A61F 2/0009; A61F
13/023; A61F 2013/00574; A61H
2201/1628; A61H 2201/165; A61H 19/50;
A61H 19/34; A61H 2201/1688; A61N
1/36007; A61N 1/36014
See application file for complete search history.

(56) References Cited

U.S. PATENT DOCUMENTS

| | | | |
|---|---|---|---|
| 9,492,260 B2 | 11/2016 | St. Anne et al. | |
| 2011/0162661 A1 | 7/2011 | St. Anne | |
| 2014/0024615 A1* | 1/2014 | London Brown | A61P 31/04 |
| | | | 514/55 |

| | | | |
|---|---|---|---|
| 2019/0231604 A1 | 8/2019 | Holm et al. | |
| 2020/0261253 A1 | 8/2020 | Moscherosch et al. | |
| 2024/0009036 A1 | 1/2024 | Jakumeit | |

FOREIGN PATENT DOCUMENTS

| | | | | |
|---|---|---|---|---|
| EP | 2544643 B1 * | 9/2018 | ......... | A61F 13/0246 |
| JP | 2001299809 A | 10/2001 | | |
| WO | 2016054292 A1 | 4/2016 | | |

OTHER PUBLICATIONS

Search Report received in International Application No. PCT/
EP2023/050595 dated Mar. 22, 2023, with translation, 7 pages.
Written Opinion received in International Application No. PCT/
EP2023/050595 dated Mar. 22, 2023, with translation, 13 pages.
Office Action received in European Application No. 23 700 771.1-
1122 dated Aug. 29, 2025, with translation, 11 pages.

* cited by examiner

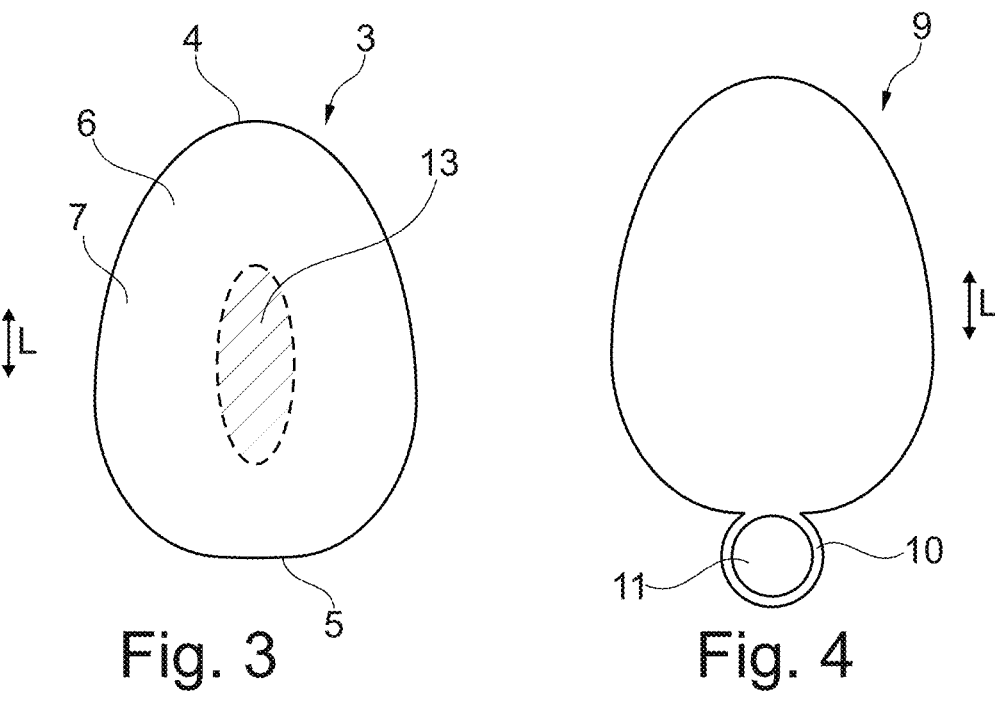
Fig. 3
Fig. 4
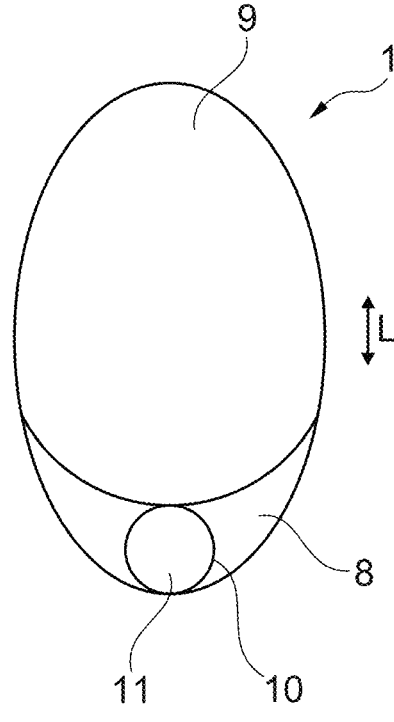
Fig. 5

PATCH FOR FEMALE GENITAL AREA

CROSS-REFERENCE TO RELATED APPLICATIONS

This application is the United States national stage entry of International Application No. PCT/EP2023/050595, filed on Jan. 12, 2023, which claims priority to German Application No. 10 2022 100 783.9, filed on Jan. 14, 2022, and which claims priority to German Application No. 20 2022 105 871.7, filed on Oct. 19, 2022. The contents of International Application No. PCT/EP2023/050595, German Application No. 10 2022 100 783.9, and German Application No. 20 2022 105 871.7 are incorporated by reference herein in their entireties.

FIELD

The present invention relates to a plaster for the female genital area comprising a plaster main film having a plaster inner surface which is covered by an adhesive layer which, during use, adheres to skin in the female genital area of a user and, when not in use, is completely covered by a cover film.

BACKGROUND

In particular for female persons and/or women and persons having female genitals, there is the risk of an infection of the urinary tract. Since women have a by far shorter urethra, they are affected by far more frequently by urinary tract infections than men.

The outer opening of the urethra (ostium urethrae externum/urethral entrance) is located between the labia minora, directly beneath the clitoris and, thus, in front of the vaginal entrance.

Infections of the efferent urinary tract which includes the renal pelvis, the ureter, the urinary bladder and the urethra (may also be referred to as "urinary tract infections") are usually caused by bacteria, wherein also viruses, fungi and other parasites may infest the urinary tract. The respective pathogens usually penetrate from the urinary tract orifice into the urethra and from there into the urinary bladder, the urethra and the urinary bladder forming the lower urinary tract. An infection of the lower urinary tract is referred to as urethritis (inflammation of the urethra) or as cystitis (inflammation of the urinary bladder) depending on the focus of infection. From the urinary bladder, the pathogens can pass further into one or both ureters and from there into the left and/or the right kidney. The two kidneys, the renal pelvis and the two ureters form the upper urinary tract. An infection of the renal pelvis is referred to as pyelonephritis and an infection of the ureters is referred to as urethritis.

Most urinary tract infections result from a transmission of pathogens which naturally occur in the intestine, such as *Escherichia-coli* bacteria, from the anus via the urinary tract orifice to/via the urethra into the urinary bladder.

Recurring urinary tract infections can also occur when *Escherichia-coli* bacteria dormant in the wall of the urinary bladder are reactivated. One of the possible triggers for the reactivation is the bacterium *Gardnerella vaginalis* which occurs in small bacterial counts in the vaginal flora and is known as a causer of vaginitis and in this case acts as an indirect trigger. It has turned out that in particular during sexual intercourse the risk of the transmission of pathogens such as *Escherichia-coli* bacteria, *Gardnerella vaginalis*, via the urinary tract orifice into the urinary tract and, thus, also the risk of a urinary tract infection is increased. If the pathogens enter into the urinary tract, they will strongly reproduce and, in so doing, will further ascend inside the urinary tract. This results in the inflammation of the urinary tract and causes one or more of the above-mentioned infections (in parallel or sequentially to each other).

In order to prevent infections in the female genital area, a vaginal plaster was suggested already. In this context, the document EP 2 544 643 B1 describes a vaginal plaster which is intended to prevent external fluid from penetrating the vagina through the vaginal entrance in a humid external environment, e.g., in the swimming pool or in the sauna. In the middle, the plaster includes a pad which contains a hygiene disinfectant and corresponds to the labia minora, and at the edge on the inner surface it includes a flexible self-adhesive film provided with a peel-off film to stick the plaster to the outer female genitals and to the surrounding skin. The plaster is dimensioned so that it covers, inter alia, the labia minora, the clitoris, the urinary tract orifice, the vaginal entrance and possibly the anus.

Consequently, covering the vaginal entrance is essential for the vaginal plaster of EP 2 544 643 B1. The vaginal plaster prevents only insignificantly, particularly when it covers also the anus, pathogens from penetrating from the anus via the urinary tract orifice into the urinary tract. It is a drawback that a hygiene disinfectant as contained in the pad of the vaginal plaster is harmful to the vaginal flora and can disturb the pH balance of the vaginal flora and, consequently, promote infections.

SUMMARY

With this in mind, it is the object of the present invention to provide a plaster that solves the above-described problems. In particular, a plaster which significantly minimizes the risk of a urinary tract infection is intended to be provided.

The plaster according to the invention is a (protective) plaster for use in the female genital area comprising a plaster main film, specifically polyurethane film, which has a plaster inner surface covered by an adhesive layer, specifically a hypoallergenic polyacrylate adhesive or a silicone adhesive, which, during use, adheres to skin in the female genital area of a user and, when not in use, is completely covered by a cover film. The plaster main film is dimensioned and designed so that, during use, it surrounds the user's urinary tract orifice completely while enclosing particularly at least a major part (more than half of the surface area) of the labia majora and minora of the user, and at the same time leaves open and, resp., does not cover the user's vaginal entrance.

Consequently, such a plaster covers the urinary tract orifice and, at the same time, leaves open the vaginal entrance of a user. Thus, the plaster as a physical barrier protects the urinary tract orifice from the penetration of pathogens. At the same time, the vaginal entrance of the user is free so that the plaster can be worn during sexual intercourse. Since particularly in this context plenty of pathogens may enter into the urinary tract orifice, the plaster according to the invention protects the user very efficiently against urinary tract infections.

More precisely, the plaster and, above all, the plaster main film is provided and designed to cover, depending on the size of the vulva, also part of the mons pubis (mons pubis), a major part of the (outer) labia majora, a major part of the (inner) labia minora, the clitoris, the urethra and the urinary tract orifice, resp., and the labia (majora and minora) at a level of the vaginal vestibule (vestibulum) and not to cover the vaginal entrance. The plaster and, resp., the plaster main film covers the labia majora up to the level of the vaginal vestibule. In other words, during use, the plaster main film covers a major part of the vulva (the outer female genital organ) of the user while leaving open the user's vaginal entrance. During use, the plaster and, resp., the plaster main film does not completely cover in particular the labia majora and the labia minora as well as the mons pubis of the user.

Advantageous configurations of said plaster are explained in detail below.

Advantageously, the plaster includes an (at least outwardly non-adhesive) stimulating element which is designed to contact and stimulate the labia minora and/or the clitoris of the user and is arranged (centrally) on the plaster inner surface. In particular, the (elongated) stimulating element is arranged at a portion of the plaster inner surface which, during use, faces the labia minora (at least partially) and/or the clitoris (completely). Accordingly, the stimulating element can rest on the plaster inner surface or can be integrated in the (multilayer) plaster main film. In each case, it is important that the stimulating element is arranged at a position of the plaster main film that faces the user during use.

The stimulating element non-adhesive at least in the areas in which it contacts the user at the respective position (particularly at the labia minora and/or at the clitoris) does not adhere to the user's skin, and, thus, the user does not feel any unpleasant irritation because of adhesive. In addition, the arrangement of the stimulating element in the area of the particularly sensitive and thus delicate area of the user ensures stimulation of her sexual organs, which is possible, inter alia, also during sexual intercourse. The stimulating element thus can trigger a pleasant feeling for the user. As a result, the user likes to apply the plaster, as the plaster according to the invention is comfortable to wear, particularly due to the integrated stimulating element.

Preferably, the stimulating element is integrated fixedly or movably into the (multilayer) plaster main film. For example, the stimulating element is an integral part of the plaster main film or the adhesive layer and is designed by deforming the plaster main film or the adhesive layer.

It is of advantage when the stimulating element rises from the plaster inner surface in the height direction of the plaster and is an object body having a rounded outer contour which is harder and/or more stable than the plaster main film.

A stimulating element designed in this way can be felt particularly well by the user and, therefore, is well suited to stimulate the user in the genital area, particularly at the labia minora and/or at the clitoris. The rounded outer contour ensures a pleasurable feeling for the user and prevents the skin contacting the stimulating element from being injured.

An advantageous aspect of the plaster relates to the fact that the stimulating element protrudes beyond the adhesive layer viewed in the height direction of the plaster. In addition, the stimulating element can be formed separately from the plaster main film, may be made of the same material as the plaster main film or as the adhesive layer, and/or can be integrated in the plaster main film. A predetermined shape can be imparted to the stimulating element, which is manufactured, for example, of the same material as the adhesive layer or the plaster main film, by means of a pressure or heat process. When the stimulating element is made of the same material as the adhesive layer, viz. is designed as a hardened adhesive area, said area which was adhesive before was made non-adhesive by neutralizing the adhesive or the adhesive layer (e.g., by treatment with UV light).

During use, such a stimulating element comes into direct contact with the user's genital area, as it protrudes beyond the adhesive layer. By designing the stimulating element separately or by deformation of the plaster main film or the adhesive layer or any other carrier layer of the plaster main film, it is easy to manufacture and subsequently to connect to the plaster main film.

The plaster inner surface can be provided to have a non-adhesive area or an adhesive-free area in the center. Preferably, the position of the plaster inner surface that faces the ureter entrance and, resp., the urinary tract orifice during use is not covered by the non-adhesive area (but by the adhesive layer). More precisely, the non-adhesive area is adapted (or corresponds) preferably in its size and its shaping, specifically with respect to its length, to the (average) size, specifically length, and shaping of the labia minora, specifically the clitoris, of the user, wherein the stimulating element is arranged at least on a portion of the non-adhesive area. In other words, a non-adhesive area which, during use, faces the labia minora and/or the clitoris is located in the area of the plaster inner surface. The stimulating element is located at least on a portion of said non-adhesive area.

Due to the non-adhesive area which, during use, should cover at least the labia minora (at least partially) and specifically the clitoris (completely), the plaster does not adhere to this particularly sensitive area. In this way, the clitoris is protected, on the one hand, against contacting the adhesive layer. On the other hand, the skin of the clitoris is not irritated when the plaster is removed. It is particularly helpful when the stimulating element is arranged in this non-adhesive area, as during use the latter is arranged level with the erogenous zone particularly susceptible to stimulation of the labia minora and/or the clitoris.

It is of particular advantage when only the portion of the non-adhesive area which is arranged, during use, in the area and, resp., level with the user's clitoris includes the stimulating element. When the stimulating element is provided exactly in this area of the plaster, the stimulating element can efficiently stimulate the user at this particularly erogenous point.

Hence it is possible that the non-adhesive area is divided into two: the non-adhesive area is divided into a first portion which, during use, faces the clitoris and includes the stimulating element and into a second portion which includes no stimulating element (and faces only the labia minora but not the clitoris).

Moreover, it is useful when the stimulating element is connected directly and stationarily, in particular affixed, to the non-adhesive area. In particular, the stimulating element is designed separately from the plaster main film in this case. Alternatively, the stimulating element is designed as an integral part of the plaster main film or the adhesive layer by deformation the plaster main film or the adhesive layer or any other carrier layer of the plaster main film.

In this way, the stimulating element can be connected to the non-adhesive area and, resp., to the plaster main film in an inexpensive, simple and quick manner and requires no complicated and costly manufacturing steps.

It can further be provided that at least partially, as viewed in the height direction of the plaster, above the non-adhesive area an additional film is arranged which together with the non-adhesive area forms an outwardly closed cavity in which the stimulating element is arranged, in particular to be freely movable. The additional film can be designed as a part of the (multilayer) plaster main film or separately therefrom.

The cavity allows the stimulating element to be movable relative to the plaster main film (and to the additional film). The free mobility of the stimulating element within the cavity allows the stimulating element to move also relative to the user's genital area during use. This can stimulate the user particularly strongly. The additional film prevents direct contact between the user's skin and the stimulating element. Thus, the user's skin can be protected in the particularly sensitive area of the labia minora and/or the clitoris.

In addition, it is possible that the cavity is filled with a, preferably medically approved, liquid or with gas, specifically air.

If the cavity is filled with air, the cavity can be easily filled. If the cavity is filled with liquid, the stimulating element moves more slowly inside the cavity than if the latter is filled with a gas. This slower movement of the stimulating element can stimulate the user particularly intensely.

Preferably, the additional film is tightly connected to the non-adhesive area. This prevents liquid from escaping from the cavity.

It is particularly useful when at least the portion of the non-adhesive area on which the at least one stimulating element is arranged, but in particular the complete non-adhesive area and, resp., the stimulating element itself is positioned relative to the plaster main film so that it does not cover the user's urinary tract orifice during use.

In this way, the stimulating element is prevented from getting in contact with the user's urinary tract orifice.

Moreover, it is advantageously provided that the whole plaster inner surface, preferably the whole adhesive surface, preferably the non-adhesive area, in particular a portion of the non-adhesive area at which no stimulating element is arranged, is provided with a moisture-absorbing hydrophilic substance (in the form of solid particles or in the form of a liquid).

Those particles can absorb moisture, specifically vaginal secretion which is present between the user's skin and the plaster, particularly well. This increases the comfort and wearing time of the plaster and, resp., the plaster main film.

As an alternative, it is conceivable that the adhesive layer covers the whole plaster inner surface, but in the portion which during use typically covers the labia minora, specifically the clitoris, moisture-absorbing hydrophilic particles are arranged on the adhesive layer. Consequently, the portion of the plaster inner surface in which the moisture-absorbing hydrophilic particles are present again forms a non-adhesive area. In said area, also the at least one stimulating element can be arranged. Further, the stimulating element can be provided to be hemispherical, almond-shaped, dome-shaped, drop-shaped, rotation-ellipsoidal, annular or spherical.

A stimulating element shaped in such way is easy to manufacture and, thus, inexpensive and particularly efficient in its stimulating effect.

In this context, it is useful, if the stimulating element itself is connected directly to the non-adhesive area and, resp., the plaster inner surface, to select the hemispherical shape, almond shape or circular shape for the stimulating element. If the stimulating element is provided inside the cavity and is freely movable relative to the plaster main film, alternatively also the spherical shape can be selected for the stimulating element.

It is useful when a unit formed of the plaster main film and the adhesive film is variable in its thickness. In a preferred case, the plaster main film may have a uniform thickness and the thickness of the adhesive layer can vary. As an alternative, the plaster main film may have a variable thickness and the adhesive layer can have a uniform thickness. In particular, it is useful when the thickness of the adhesive layer is increased around a point of the plaster inner surface facing the urinary tract orifice during use.

It is of advantage when the material thickness of the unit of the plaster main film and the adhesive layer increases, specifically continuously, starting from the upper longitudinal end of the plaster main film to the lower longitudinal end of the plaster main film.

In addition, it is useful when a plaster outer surface of the plaster main film has a planar/flush/flat design. Accordingly, there are no protrusions projecting from the plaster outer surface which might be disturbing during use, particularly during sexual intercourse.

It is particularly advantageous when the plaster further includes a stabilizing film which, when not in use, covers, specifically completely, a particularly non-adhesive plaster outer surface main film facing the plaster inner surface and being identical to it in shape, and the stabilizing film is designed to be stiffer and/or more stable, specifically made of a stiffer material, than the plaster main film and is prepared and designed to stabilize the plaster main film for being arranged around the urinary tract orifice.

The plaster main film itself is manufactured of a very flexible material which can properly adjust to the structure in the female genital area. For this reason, the plaster is not easy to position between the mons pubis and the vaginal entrance, however. Therefore, the stabilizing film temporarily stiffens the plaster main film to enable the plaster main film to be easily positioned and aligned relative to the female genital area. As soon as the desired position of the plaster main film around the urinary tract orifice is found, while leaving open the vaginal entrance, the stabilizing film is removed from the plaster main film.

It is very helpful when a positioning and removing device that projects from the stabilizing film beyond the periphery of the plaster main film and/or the stabilizing film and is particularly ring-shaped is attached/fixed to the stabilizing film.

By means of the positioning and removing device, the plaster and, resp., the plaster main film can be positioned very easily and properly in the female genital area (at the vulva). In addition, by means of the positioning and removing device, the stabilizing film can be removed very easily and quickly from the plaster main film. As the positioning and removing device projects beyond the periphery of the stabilizing film and/or the plaster main film, the positioning and removing device can be gripped particularly easily.

It is further efficient when the positioning and removing device includes a, specifically through-, opening which is dimensioned and shaped so that the user can reach into the opening with at least one of her fingers, particularly the middle or index finger.

The positioning and removing device is particularly easy to grip by means of the opening.

In a particularly preferred design, the positioning and removing device is ring-shaped. A ring can be seized very easily. As an alternative, the positioning and removing device could also be oval, rectangular, triangular, trapezoidal or polygonal in its geometrical shape.

The positioning and removing device can further be provided to be arranged at a position of the stabilizing film which covers a lower longitudinal end of the plaster main film facing the vaginal entrance during use.

With the aid of the positioning and removing device arranged in this way, the lower longitudinal end of the plaster and, resp., the plaster main film can be positioned directly in front of the vaginal entrance and, thus, on the labia majora level with the vaginal vestibule, and starting from there the plaster and, resp., the plaster main film can be applied to the skin in the female genital area as above described. Consequently, when the positioning and removing device is arranged at the position of the stabilizing film which covers the lower longitudinal end of the plaster main film, the plaster can be aligned and positioned relative to the vulva particularly efficiently and easily.

In this context, it is useful when the positioning and removing device is stiffer and/or more stable than the stabilizing film.

In this way, the positioning and removing device can be used very efficiently to position the plaster on the user and to remove the stabilizing film from the plaster main film.

The positioning and removing device can be materially connected with the stabilizing film, if e.g. the positioning and removing device and the stabilizing film are made of different materials, or can be formed in one piece with the stabilizing film.

Moreover, the positioning and removing device can be provided to be designed and prepared (to be gripped by the user and), as a positioning device, to enable positioning of the plaster main film on (the skin in the female genital area of) the user and, as a removing device, to enable removal of the stabilizing film from the plaster outer surface after the plaster main film has been positioned on (the vulva of) the user.

Therefore, with the aid of the positioning and removing device it is possible to position the plaster and, resp., the plaster main film particularly easily and efficiently on the user's vulva. Further, with the aid of the positioning and removing device it is possible to remove the stabilizing film very easily and quickly from the plaster main film.

It makes sense to use the positioning and removing device so that the user inserts a finger, preferably the index or middle finger, into the opening of the positioning and removing device. Then said finger feels for the vaginal entrance to affix starting from there the lower longitudinal end of the plaster main film in the direction of the mons pubis. The finger inserted into the positioning and removing device removes, by applying tension to the positioning and removing device, the stabilizing film from the plaster main film as soon as the latter was affixed to the user's skin as desired.

The positioning and removing device can be designed so that it is anchored in the vaginal entrance and includes a tab/peel-off aid attached thereto which is connected to the stabilizing film and by means of which the stabilizing film can be peeled off the plaster main film toward the mons pubis.

Preferably, the cover film is formed in one piece, covers the whole plaster inner surface and moreover protrudes with a portion beyond the lower longitudinal end of the plaster main film.

Because the cover film protrudes beyond the outer periphery of the plaster main film at least at one point, it is particularly easy to grip and, thus, to peel off and remove from the adhesive layer.

In addition, it is conceivable that the cover film is identical in shape to the plaster inner surface, apart from the portion protruding beyond the lower longitudinal end of the plaster main film which in turn overlaps the opening the of positioning and removing device. Preferably, the cover film is not bonded or otherwise fixed to the positioning and removing device. In other words, the cover film is preferably provided to loosely overlap the opening of the positioning and removing device.

The cover film can be peeled off the adhesive layer particularly easily due to its overlapping with the opening of the positioning and removing device: the user can insert her finger through the opening in the direction of the cover film and lift/press the latter off the positioning and removing device. In the next step, the user thus can grip said portion of the cover film lifted off the positioning and removing device very easily and, subsequently, peel it off the adhesive layer. This facilitates the use and improves the handling of the plaster.

Of advantage, the cover film can be provided to extend in the longitudinal direction from an upper longitudinal end of the plaster main film (that faces the mons pubis during use) up to a portion of the positioning and removing device maximally distant from the upper longitudinal end of the plaster main film in the longitudinal direction, the positioning and removing device itself being arranged at a lower longitudinal end opposite to the upper longitudinal end viewed in the longitudinal direction.

Thus, the cover film extends along, but not beyond, the whole plaster length. The plaster of this type is therefore handy and easy to handle.

An advantageous aspect of the plaster relates to the fact that a length of the plaster main film corresponds to an average vertical distance between the mons pubis and the end of the vaginal entrance facing the mons pubis, and during use an upper longitudinal end of the plaster main film faces the mons pubis and a lower longitudinal end of the plaster main film faces the vaginal entrance.

The averaged/mean length of the labia majora of a plurality of women ranges from 60 mm to 120 mm. Thus, the length of the plaster main film ranges from 40 mm to 100 mm. The plaster main film can be arranged, depending on the anatomy, on the user's vulva so that at least the urinary tract orifice is covered and the vaginal entrance is left open. For example, excess film can be moved toward the mons pubis, i.e., in the case of persons with smaller measurements, the plaster covers more of the mons pubis.

When the plaster has such a length and the upper longitudinal end of the plaster main film faces the mons pubis and the lower longitudinal end of the plaster main film faces the vaginal entrance, the plaster safely covers the urinary tract orifice and leaves open the vaginal entrance during use.

It is useful when the material thickness of the plaster main film increases, particularly continuously, from its upper longitudinal end to its lower longitudinal end. Alternatively, the material thickness of the plaster main film can be continuous and the adhesive layer can increase, particularly continuously, from the upper longitudinal end of the plaster main film to the lower longitudinal end of the plaster main film. As an alternative, the thickness of the plaster main film and the thickness of the adhesive layer may be substantially, and the thickness of the adhesive layer may be increased only around the area which during use faces the user's urinary tract orifice.

In particular during sexual intercourse, the area in the lower longitudinal end of the plaster is heavily strained by friction. If the plaster is reinforced in this area, particularly around the urinary tract orifice, as compared to the remaining plaster, the plaster is more stable and, thus, less sensitive to friction. Hence it is unlikely that the plaster will come off (coil up), tear or be damaged otherwise despite increased friction at the correspondingly reinforced position.

Moreover, the plaster main film may be provided to be wider in the area of the lower longitudinal end than in the area of the upper longitudinal end.

In this way, the shape of the plaster follows the natural shaping of the user's labia majora and, therefore, can be affixed particularly well and safely to the skin of said labia majora.

It is moreover possible that the lower longitudinal end of the plaster main film extends straightly and the remaining outer periphery of the plaster main film is (convexly) curved.

The lower longitudinal end of the plaster main film rests on the labia majora level with the vaginal vestibule. Hence, if the lower longitudinal end of the plaster main film has a straight design and extends straightly, it can rest particularly safely and tightly on the labia majora level with the vaginal vestibule. Thus, the straightly extending lower longitudinal end supports a secure fit of the plaster in the female genital area. The plaster is optimally adjusted, via the other (convex) curvature of the outer periphery of the plaster main film, to the shape of the labia majora to which the plaster mainly adheres.

It is particularly useful when the length of the straight portion of the lower longitudinal end of the plaster main film corresponds at least to the average width of the labia majora in this area. The length of the straight portion of the lower longitudinal end of the plaster main film is between 20 mm and 50 mm, preferably between 20 mm and 40 mm, specifically preferably is 30 mm.

Accordingly, the optimum adhesion of the plaster main film can be safeguarded by means of the adhesive layer to the labia majora level with the vaginal vestibule in the area of the lower longitudinal end.

Advantageously, it is moreover provided that a maximum width of the plaster main film corresponds to an average maximum horizontal distance between the outer edges of the labia majora facing away from each other, and thus in particular the maximum width of the plaster main film is between 50 mm and 70 mm, preferably between 56 mm and 66 mm and particularly preferably is 59 mm, and the plaster main film in the width direction extends at least between the outer edges of the user's labia majora facing away from each other.

The average maximum horizontal distance between the outer edges of the labia majora facing away from each other corresponds to a mean value of the corresponding distance for a plurality of women. In other words, the maximum width of the plaster is the width of an average vulva.

Optimally, the plaster at its widest point therefore is as wide as the average maximum horizontal distance between the outer edges of the labia majora facing away from each other. Thus, the plaster and, resp., the plaster main film can rest optimally on the labia majora.

As an alternative to the cover film formed in one piece, the cover film may also be in two parts, a first cover film portion covering a portion of the adhesive layer of the plaster main film and a second cover film portion covering the remaining adhesive layer. In particular, the second cover film portion also covers a portion of the first cover film portion. In this way, the second cover film portion can be easily gripped for removal and in this way the (two-part) cover film can be easily peeled off the adhesive layer.

Preferably, the stabilizing film and possibly also the cover film (if the cover film is in two parts) is identical in shape to the plaster main film. In this way, the stabilizing film stabilizes the plaster main film optimally. The (two-part) cover film efficiently protects the adhesive layer when it has the same shape and size as the plaster main film.

In particular, the plaster main film and, preferably, also the cover film and the stabilizing film (apart from the straight portion of the lower longitudinal end) are egg-shaped. An egg-shaped plaster main film is adapted particularly well to the anatomy of the vulva, particularly to the contours of the labia majora. When the plaster main film is egg-shaped, the upper longitudinal end of the plaster main film constitutes the (rounded) egg tip. The upper longitudinal end may have a fraying adjacent to the egg tip or differently shaped (such as heart-shaped, etc.) projections. The lower longitudinal end of the plaster main film forms the round bodied end of the egg opposite to the egg tip, however having a straightly extending portion.

As an alternative to the egg shape, the plaster main film may be oval, circular, rectangular, triangular, trapezoidal or polygonal in shape, each having rounded corners. Rounded corners prevent premature, unintentional detaching of the plaster main film, as they reduce or prevent coil-up of the plaster main film.

It is particularly useful when the material of the plaster main film is (highly) flexible, water- and germproof as well as permeable to water vapor and gas, specifically permeable to oxygen. A plaster main film having those material properties is very comfortable to wear. The (high) permeability to water vapor of the plaster main film helps prevent moisture from accumulating between the user's skin and the plaster and, resp., the plaster main film and reduce the risk of macerations (moistening of the skin). Since the film is highly flexible, it fits to the user's skin like a second skin.

In particular, the adhesive force or adhesive effect of the adhesive layer is moreover at least so great that the plaster main film still adheres to the user's skin even during friction in a sexual intercourse which applies a dynamic shear stress to the adhesive layer. The adhesive force at the same time should not be so great/strong that removing or peeling off the plaster main film results in skin irritations or even injuries of the user.

Preferably, the stabilizing film can be provided to include an adhesive layer on the side facing the plaster outer surface to be temporarily connected to the plaster outer surface which itself is non-adhesive. The advantage resides in the fact that the stabilizing film adheres safely and tightly to the plaster main film when the plaster is not in use. During use, the exposed plaster outer surface is not sticky so that nothing can adhere to the plaster outer surface.

In particular, the plaster main film, sensibly also the stabilizing film and/or the cover film, has a smooth surface and a smooth and rounded outer periphery. This reduces the friction on the user's skin.

A particularly preferred plaster therefore includes a plaster main film including a plaster inner surface, which during use faces a user and is partially covered with an adhesive layer, and a plaster outer surface which is opposite to the plaster inner surface and, during use, faces away from a user. Further, the plaster has a stabilizing film comprising a positioning and removing device attached thereto and projecting beyond the periphery of the stabilizing film and preferably also of the plaster main film, the stabilizing film covering, particularly completely, the plaster outer surface (when not in use). Furthermore, the plaster includes a cover film which covers, particularly completely, the adhesive film of the plaster main film, but which is removed from the plaster main film during use.

Such plaster is used as follows:

Initially the cover film is peeled off the adhesive layer of the plaster main film. Then the plaster inner surface of the plaster main film to the plaster outer surface the stabilizing film adheres is arranged or positioned at the user's vulva (around the user's urinary tract orifice) relative to the vulva by means of a finger inserted into the positioning and removing device. In doing so, the vaginal entrance is felt for by the finger so as to arrange and stick from there the lower longitudinal end of the plaster main film by means of the adhesive film to the labia majora level with the vaginal vestibule and to press and consequently stick the remaining plaster main film via the adhesive layer to the vulva, specifically to the labia majora, in the direction of the mons pubis. Finally, the stabilizing film is peeled off and removed from the plaster main film in the direction of the mons pubis by means of the positioning and removing device.

BRIEF DESCRIPTION OF THE DRAWINGS

FIG. 3 shows a top view onto a plaster inner surface of a plaster main film of the plaster;

FIG. 4 shows a top view onto a stabilizing film of the plaster;

FIG. 5 shows a rear view of the plaster including a cover film according to a second alternative;

DETAILED DESCRIPTION

In the following, aspects of the present disclosure will be described on the basis of the related Figures. The shown aspects are only exemplary and can be combined with each other, as far as technically reasonable.

Figure 1:
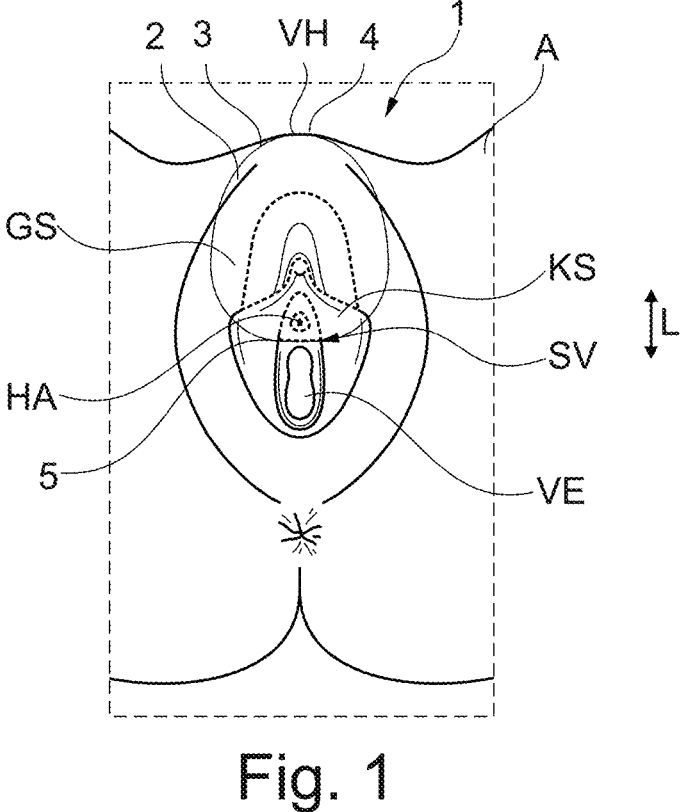
FIG. 1 shows a top view of a plaster in a state in which the plaster is arranged on a user.

FIG. 1 illustrates a top view of a plaster 1 during use in which the plaster 1 is applied to a user A. More precisely, in this view only a plaster outer surface 2 of a plaster main film 3 of the plaster 1 facing away from the user A is visible. Accordingly, is clearly visible that the plaster 1 leaves open and, resp., does not cover the vaginal entrance VE of the user A. More precisely, an upper longitudinal end 4 of the plaster main film 3 in the longitudinal direction L is adjacent to the mons pubis VH, and a lower longitudinal end 5 of the plaster main film 3 in the longitudinal direction L extends transversely over the labia majora GS level with the vaginal vestibule SV of the user A. On its surface facing the user A, the plaster main film 3 forms a plaster inner surface 6 which is not visible in this view (but is shown in FIG. 3). On said plaster inner surface 6 an adhesive layer 7 (also not visible here) is provided. By means of the adhesive layer 7, the plaster main film 3 adheres to the skin, but not to the mucosa, the vulva and around the urinary tract orifice HA. More precisely, the plaster main film 3 sticks to the skin, and not the mucosa, of the (outer) labia majora GS and follows the contour thereof due to its shaping. The lower longitudinal end 5 of the plaster main film sticks to the labia majora GS level with the vaginal vestibule SV.

It can be seen that the plaster main film 3 is egg-shaped, wherein the narrow tip of the egg forms the upper longitudinal end 4 of the plaster main film 3 and the end of the egg remote from the narrow tip forms the lower longitudinal end 5 of the plaster main film 3. In order to adhere as wrinkle-free as possible to the labia majora GS level with the vaginal vestibule SV, the outer periphery of the plaster main film 3 is designed to be straight in the area of the lower longitudinal end 5. In other words, at least the portion of the lower longitudinal end 5 which is in contact with the labia majora level with the vaginal vestibule SV extends straightly. The remaining outer periphery of the plaster main film 3 is (convexly) curved to be adapted optimally to the shape of the labia majora GS.

Figure 2:
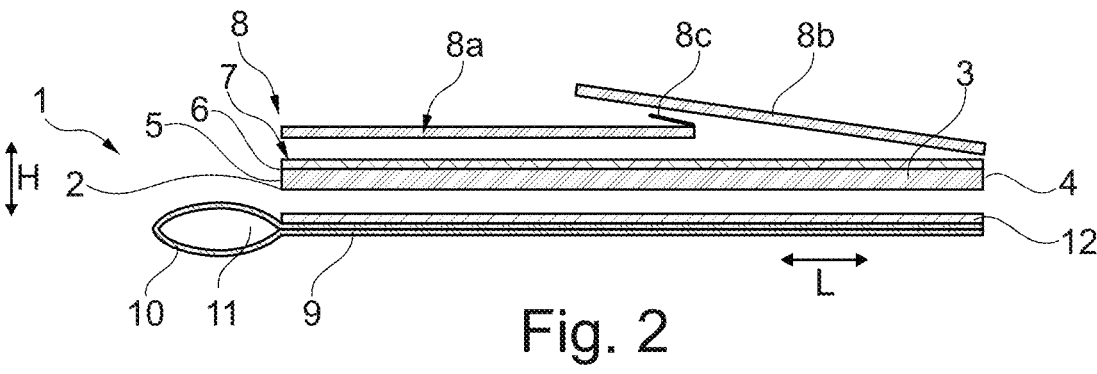
FIG. 2 shows an exploded view of a longitudinal section view of the plaster including a cover film according to a first alternative.

FIG. 2 is an exploded view of a longitudinal section view of the plaster 1 including a cover film according to a first alternative. It can be seen that, apart from the plaster main film 3, the plaster 1 also has a cover film 8 of the first alternative as well as a stabilizing film 9. Accordingly, FIG. 2 illustrates the plaster 1 when it is not in use, i.e., before use. The cover film 8 completely covers the adhesive layer 7 arranged on the plaster inner surface 6. Hence, the cover film 8 prevents the adhesive layer 7 from unwantedly adhering to other objects before the plaster 1 is used as intended in the female genital area (on the vulva). Thus, the cover film 8 protects the adhesive layer 7 also from wear.

In this case, the cover film 8 is formed in two parts according to a first alternative. A first cover film portion 8a of the cover film 8 extends from the lower longitudinal end 5 to the upper longitudinal end 4 and covers at least a lower (longitudinal) half of the plaster inner surface 6. The end portion of the first cover film portion 8a facing the upper longitudinal end 4 advantageously is turned/folded over itself toward the lower longitudinal end 5 to form a grip tab 8c. Said grip tab 8c which is formed in one piece with the first cover film portion 8 and forms a portion of the first cover film portion 8a facilitates removal of the first cover film portion 8a from the adhesive layer 7.

A second cover film portion 8b of the cover film 8 extends from the upper longitudinal end 4 to the lower longitudinal end 5 and covers the remaining plaster inner surface 6 (the upper longitudinal half thereof) and at least a portion (facing the upper longitudinal end 4) of the first cover film portion 8a as seen in the height direction H. In other words, as seen in the height direction H, a portion of the second cover film portion 8b overlaps or protrudes beyond the first cover film portion 8a. To remove the cover film 8 from the adhesive layer 7, the user A can easily grasp the portion of the second cover film portion 8b overlapping/protruding from the first cover film portion 8a and, thus, can initially peel the second cover film portion 8b off the adhesive layer 7. After that, the user A can grasp the first cover film portion 8a, particularly the grip tab 8c thereof, and also peel it off the adhesive layer 7.

The stabilizing film 9 completely covers the plaster outer surface 2. The stabilizing film 9 is only used to dimensionally stabilize the flexible plaster main film 3. If the plaster main film 3 is appropriately applied in the female genital area (after removing the cover film 8 from the adhesive layer 7), the stabilizing film remains on the plaster main film 3 until the plaster main film 3 was applied completely and satisfactorily to the skin of the vulva of the user A, as described in connection with FIG. 1. Only then is the stabilizing film 9 removed from the plaster outer surface 2 of the plaster main film 3.

At the position of the stabilizing film 9 covering the lower longitudinal end 5 of the plaster main film 3, a positioning and removing device 10 extends from (the outer periphery) of the stabilizing film 9. Thus, the positioning and removing device 10 protrudes beyond the periphery of the stabilizing film 9 as well as from the periphery of the plaster main film 3. The positioning and removing device 10 is ring-shaped in this case. Therefore, the positioning and removing device 10 has a central opening 11. The opening 11 is dimensioned and shaped so that the user A can insert at least one of her fingers, specifically the index or middle finger, into the opening 11.

To apply the plaster 1 to the user A, the user A inserts at least one finger into the opening 11 of the positioning and removing device 10 (after having already removed the cover film 8 from the adhesive layer 7). Then said finger feels for the vaginal entrance VE. Starting from the felt vaginal entrance VE, the lower longitudinal end 5 of the plaster main film 3 is then affixed via the adhesive layer 7 to the skin in the area of the vaginal vestibule SV. From there, the remaining plaster main film 3 is affixed, preferably under tension to avoid wrinkling, to the skin of the labia majora GS so that the plaster 1 is oriented and positioned, as in FIG. 1, relative to the (vulva of the) user A. When the plaster 1 is appropriately affixed to the desired position of the user A, the stabilizing film 9 is removed from the plaster outer surface 2 of the plaster main film 3 by pulling the positioning and removing device 10 in the direction of the mons pubis VH. Thus, the plaster 1 is finally arranged on the user A (as shown in FIG. 1, too).

To prevent the plaster 1 from adhering to objects surrounding the user A such as her clothes and particularly her underwear, the plaster outer surface 2 is non-adhesive. Therefore, for temporarily fixing the stabilizing film 9 to the plaster outer surface 2, the stabilizing film 9 is provided with an adhesive layer 12.

FIG. 3 is a top view onto the plaster inner surface 6 of the plaster main film 3. The plaster inner surface 6 is completely covered by the adhesive layer 7 except for a non-adhesive area 13, which in this case is a portion of the plaster inner surface 6. The adhesive area 13 is arranged at a central area of the plaster inner surface 6. The non-adhesive area 13 is substantially oval and thus takes a stylized shape of the (inner) labia minora KS. The non-adhesive area 13 is thus located at such a position of the plaster inner surface 6 which during use contacts the labia minora KS and, particularly, the clitoris of the user A. During use, the non-adhesive area 13 thus also, and preferably only, spans the clitoris of the user A.

FIG. 3 clearly shows the egg shape of the plaster main film 3. Further, also the straight extension of the lower longitudinal end 5 can be seen. Moreover, it can also be seen that the upper longitudinal end 4 forms the egg tip.

FIG. 4 is a top view onto the stabilizing film 9 of the plaster 1. The stabilizing film 9, too, is egg-shaped. Advantageously, the stabilizing film 9 is sized and designed just as the plaster main film 3. It can further be seen from FIG. 4 that the ring-shaped positioning and removing device 10 is arranged on the stabilizing film 9. In this case, the positioning and removing device 10 is formed in one piece with the stabilizing film 9 (made of the same material). However, the positioning and removing device 10 is designed to be more stable and stiffer than the stabilizing film 9 due to material accumulation. The positioning and removing device 10 is arranged on the (straightly extending) portion of the stabilizing film 9 which is designed to cover the lower longitudinal end 5 (not visible here) of the plaster main film 3.

FIG. 5 is a rear view of the plaster 1 including the cover film 8 according to a second alternative. In the fore, the stabilizing film 9 including the connected positioning and removing device 10 can be seen. The cover film 8 is formed in one piece and completely covers the plaster inner surface 6 not visible here. Just as the cover film 8 of the first alternative, also the cover film 8 of the second alternative covers the adhesive layer 7 arranged on the plaster inner surface 6 completely. The outer periphery of the cover film 8 substantially corresponds to the outer periphery of the plaster main film 3 also not visible here and, resp., to the outer periphery of the stabilizing film 9 apart from a portion of the cover film 8 protruding beyond the lower longitudinal end 5 of the plaster main film 3. The cover film 8 of the second alternative is elliptical in shape. One can see that the cover film 8 is flush, at its own lower longitudinal end, with the lower longitudinal end of the positioning and removing device 10. Thus, the cover film 8 overlaps the opening 11.

Figure 6:
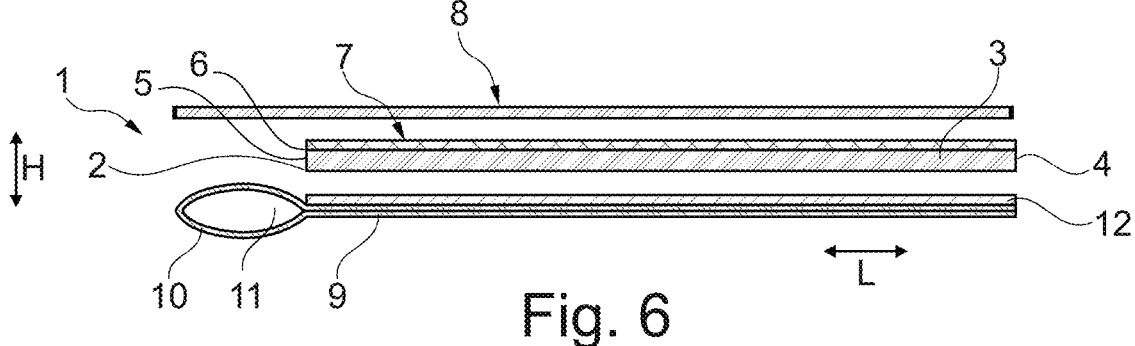
FIG. 6 shows an exploded view of a longitudinal section view of the plaster including a cover film according to the second alternative.

FIG. 6 is an exploded view of a longitudinal section view of the plaster 1 including a cover film 8 according to the second alternative. Apart from the cover film 8, said plaster 1 shown in FIG. 6 is identical to the plaster in FIG. 2. It is clear from FIG. 6 that the cover film 8 is formed in one piece. It is further clear that the longitudinal end of the cover film 8 shown on the left in FIG. 6, i.e. lower longitudinal end, extends over the positioning and removing device 10 and, thus, also over the opening 11 formed by it. The lower longitudinal end of the cover film 8 is level with the longitudinal end of the positioning and removing device 10 shown on the left in FIG. 6, i.e. lower longitudinal end, as seen in the longitudinal direction L of the plaster 1.

For removing the cover film 8 from the adhesive layer 7, the user A can easily insert her finger through the opening 11. The finger of the user A then can lift the cover film 8 from the positioning and removing device 10 in the height direction H toward the cover film 8. Said lifted portion of the cover film 8 then can be gripped and the cover film 8 can be easily removed from the adhesive layer 7 by pulling said lifted portion of the cover film 8.

Figure 7:
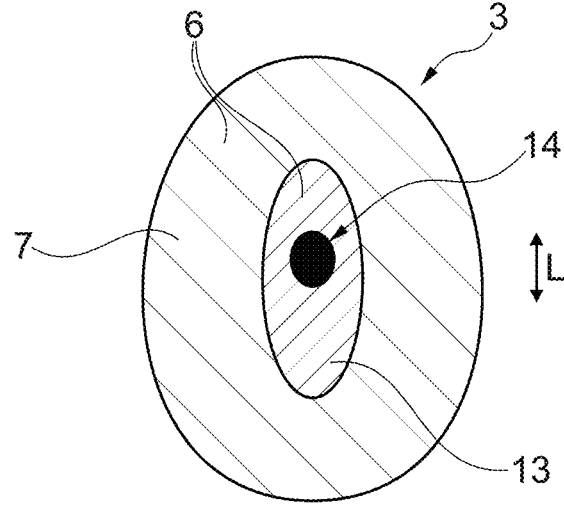
FIG. 7 shows a top view onto a plaster inner surface of a plaster main film including a stimulating element.

FIG. 7 is a top view onto the plaster inner surface 6 of the plaster main film 3 of the plaster 1 including a stimulating element 14. The stimulating element 14 is arranged on the non-adhesive area 13. In this case, the stimulating element 14 is hemispherical. The stimulating element 14 is fixed directly to the non-adhesive area 13, according to a first alternative shown here, and is thus bound and, resp., connected stationarily to the plaster film 3.

Figure 8:
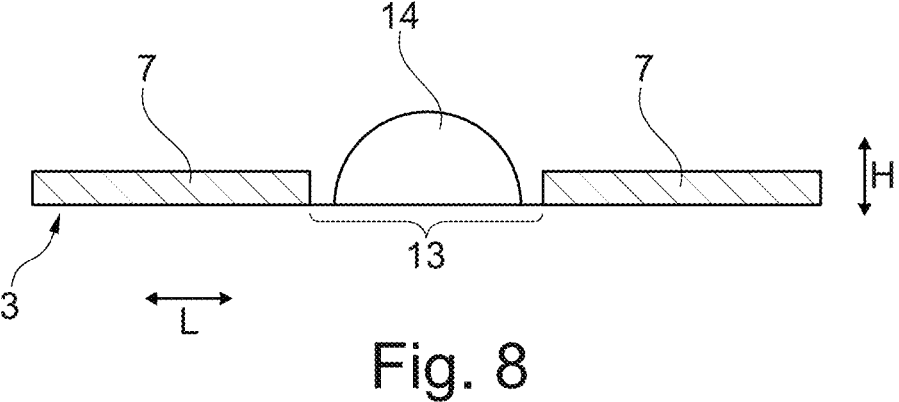
FIG. 8 shows a longitudinal section view of the plaster main film including the stimulating element.

FIG. 8 is a longitudinal section view of the plaster main film 3 including the stimulating element 14. It can be seen that the adhesive layer 7 rises from the plaster inner surface 6 in the height direction H. In the central area of the plaster main film 3, the plaster inner surface 6 includes no adhesive layer 7 and at this position forms the non-adhesive area 13. The stimulating element 14 is arranged on a portion of the non-adhesive area 13. Preferably, the stimulating element 14 is affixed to the non-adhesive area 13. The stimulating element 14 extends in the height direction H and protrudes in the height direction H beyond the adhesive layer 7 adjacent thereto.

Although not illustrated here, the adhesive layer 7 can extend over the whole plaster inner surface 6. In this case, the non-adhesive area 13 is formed by an additional non-adhesive film affixed to the adhesive layer 7 in the central area of the plaster main film 3 (not shown here).

Figure 9:
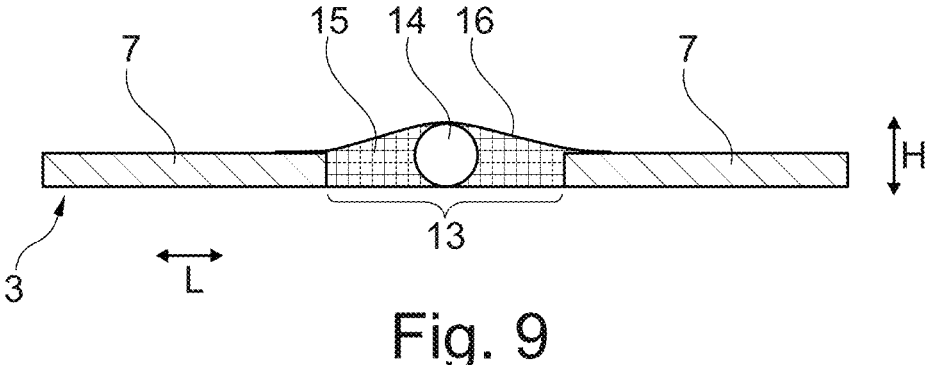
FIG. 9 shows a longitudinal section view of the plaster main film including a cavity and a stimulating element arranged therein.

FIG. 9 illustrates a longitudinal section view of the plaster main film 3 comprising a cavity 15 and a stimulating element 14 arranged therein. As in FIG. 8, in this case the non-adhesive area 13 is formed by an interruption of the adhesive layer 7 in the central area of the plaster main film 3. In this case, an additional film 16 is spanned over the whole non-adhesive area 13. The additional film 16 together with the non-adhesive area 13 forms a cavity 15. The cavity 15 is delimited by the adhesive layer 7 in the longitudinal direction L. The stimulating element 14 is located in the cavity 15. It is conceivable that the cavity 15 is filled with a liquid inside of which the stimulating element 14 can move or inside of which the stimulating element 14 floats. The stimulating element 14 is freely movable inside the cavity 15 relative to the plaster main film 3. In this case, the stimulating element 14 is formed as a sphere. In this second alternative of arranging the stimulating element 14 on the plaster main film 3, too, the stimulating element 14 protrudes beyond the adhesive layer 7 in the height direction H. The additional film 14 is flexible, i.e. it allows a movement of the stimulating element 14. As an alternative, it is conceivable that the additional film 16 protrudes beyond or spans only a portion of the non-adhesive area 13. In this case, the cavity 15 is smaller than shown in FIG. 9.

LIST OF REFERENCE SIGNS

1 plaster
2 plaster outer surface
3 plaster main film
4 upper longitudinal end of plaster main film
5 lower longitudinal end of plaster main film
6 plaster inner surface
7 adhesive layer
8 cover film
8a first cover film portion
8b second cover film portion
8c grip tab (of the first cover film portion)
9 stabilizing film
10 positioning and removing device
11 opening
12 adhesive layer
13 non-adhesive area of the plaster inner surface
14 stimulating element
15 cavity
16 additional film
A user
H height direction
L longitudinal direction
GS labia majora
HA urinary tract orifice
KS labia minora
SV vaginal vestibule
VE vaginal entrance
VH mons pubis

The invention claimed is:

1. A plaster for use in a female genital area of a user, the plaster comprising a plaster main film with a plaster inner surface that is covered at least partially by an adhesive layer which, during use, adheres to skin in the female genital area of the user and, when not in use, is completely covered by a cover film, the plaster main film being dimensioned and configured so that, during use, the plaster main film covers a urinary tract orifice of the user completely, while enclosing at least a major part of labia majora and labia minora of the user, while leaving open a vaginal entrance of the user, during use, an upper longitudinal end of the plaster main film faces a mons pubis of the user and a lower longitudinal end of the plaster main film faces the vaginal entrance, and the lower longitudinal end of the plaster main film extending straightly and an outer periphery of the plaster main film being convexly curved.

2. The plaster according to claim 1, wherein at least one protuberance is arranged on the plaster inner surface, which, during use, faces labia minora and/or a clitoris of the user, the at least one protuberance being provided to contact and stimulate the labia minora and/or the clitoris of the user.

3. The plaster according to claim 2, wherein a center of the plaster inner surface has a non-adhesive area which has a size and a shape adapted to the size and the shape of the labia minora, wherein the at least one protuberance is arranged at least on a portion of the non-adhesive area.

4. The plaster according to claim 3, wherein at least partially, as seen in a height direction of the plaster, above the non-adhesive area an additional film is arranged which together with the non-adhesive area forms an outwardly closed cavity in which the at least one protuberance is arranged.

5. The plaster according to claim 4, wherein the at least one protuberance is arranged within the outwardly closed cavity in a freely movable manner.

6. The plaster according to claim 3, wherein the at least one protuberance is directly and stationarily connected to the non-adhesive area.

7. The plaster according to claim 3, wherein at least the portion of the non-adhesive area on which the at least one protuberance is arranged, is positioned relative to the plaster main film so that the portion does not cover the urinary tract orifice of the user during use.

8. The plaster according to claim 3, wherein an entirety of the plaster inner surface is provided with a moisture-absorbing hydrophilic substance.

9. The plaster according to claim 3, wherein a size and a shape of the non-adhesive area is adapted to the clitoris of the user.

10. The plaster according to claim 3, wherein an entirety of the non-adhesive area is positioned relative to the plaster main film so that the entirety of the non-adhesive area does not cover the urinary tract orifice of the user during use.

11. The plaster according to claim 3, wherein the non-adhesive area is provided with a moisture-absorbing hydrophilic substance, and an entirety of the plaster inner surface is not provided with the moisture-absorbing hydrophilic substance.

12. The plaster according to claim 2, wherein the at least one protuberance rises from the plaster inner surface in a height direction of the plaster and is an object body having a rounded outer contour that is harder and/or more stable than the plaster main film.

13. The plaster according to claim 2, wherein the at least one protuberance protrudes beyond the adhesive layer viewed in a height direction of the plaster.

14. The plaster according to claim 2, wherein the at least one protuberance is arranged on a portion of the plaster inner surface.

15. The plaster according to claim 1, further comprising a stabilizing film which covers a plaster outer surface of the plaster main film opposite to and designed to be identical in shape to the plaster inner surface, and the stabilizing film is designed to be stiffer and/or more stable than the plaster main film and is prepared and designed to stabilize the plaster main film for arrangement on the user.

16. The plaster according to claim 15, wherein a positioning and removing device is attached to the stabilizing film, and wherein the positioning and removing device protrudes from the stabilizing film beyond a periphery of the plaster main film and/or a periphery of the stabilizing film.

17. The plaster according to claim 16, wherein the positioning and removing device includes an opening which is dimensioned and shaped so that the user can grip with at least one finger into the opening.

18. The plaster according to claim 17, wherein the cover film is identical in shape to the plaster inner surface, apart from a portion protruding beyond the lower longitudinal end of the plaster main film which, in turn, overlaps the opening of the positioning and removing device.

19. The plaster according to claim 18, wherein the cover film extends in a longitudinal direction from an upper longitudinal end of the plaster main film viewed in the longitudinal direction of the plaster to a portion of the positioning and removing device at maximum distance from the upper longitudinal end of the plaster main film, the positioning and removing device itself being arranged on the lower longitudinal end opposite to the upper longitudinal end viewed in the longitudinal direction.

20. The plaster according to claim 16, wherein the positioning and removing device is designed to be stiffer and/or more stable than the stabilizing film.

21. The plaster according to claim 16, wherein the positioning and removing device is designed and prepared to enable the plaster main film to be positioned on the user and, after positioning the plaster main film on the user, to enable the stabilizing film to be removed from the plaster outer surface.

22. The plaster according to claim 1, wherein a length of the plaster main film corresponds to an average vertical distance between the mons pubis and an end of the vaginal entrance facing the mons pubis, and is between 60 mm and 100 mm.

23. The plaster according to claim 22, wherein the length of the plaster main film is between 70 mm and 100 mm.

24. The plaster according to claim 1, wherein the cover film is formed in one piece, covers an entirety of the plaster inner surface and, in addition, by a portion protruding beyond a lower longitudinal end of the plaster main film viewed in a longitudinal direction of the plaster.

25. The plaster according to claim 1, wherein a material thickness of the adhesive layer around a position of the plaster which, during use, faces the urinary tract orifice of the user is at a maximum.

26. The plaster according to claim 1, wherein the plaster main film is wider in an area of the lower longitudinal end than in an area of the upper longitudinal end.

27. The plaster according to claim 1, wherein a maximum width of the plaster main film corresponds to an average maximum horizontal distance between outer edges of the labia majora facing away from each other, and is between 50 mm and 70 mm, and during use the plaster main film extends in a width direction at least between the outer edges of the labia majora of the user facing away from each other.

* * * * *